(12) United States Patent
Chodkowski et al.

(10) Patent No.: US 9,956,368 B2
(45) Date of Patent: May 1, 2018

(54) PATIENT INTERFACE DEVICE WITH CUSTOMIZABLE CUSHION

(71) Applicant: KONINKLIJKE PHILIPS N.V., Eindhoven (NL)

(72) Inventors: Lauren Patricia Chodkowski, Pittsburgh, PA (US); Maureen Harp, Pittsburgh, PA (US); Kevin Daniel Himes, Irwin, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 600 days.

(21) Appl. No.: 14/362,467

(22) PCT Filed: Dec. 7, 2012

(86) PCT No.: PCT/IB2012/057059
§ 371 (c)(1),
(2) Date: Jun. 3, 2014

(87) PCT Pub. No.: WO2013/088321
PCT Pub. Date: Jun. 20, 2013

(65) Prior Publication Data
US 2014/0338671 A1    Nov. 20, 2014

Related U.S. Application Data

(60) Provisional application No. 61/570,367, filed on Dec. 14, 2011.

(51) Int. Cl.
*A61M 16/06*     (2006.01)
*A61M 16/00*     (2006.01)

(52) U.S. Cl.
CPC .... *A61M 16/0622* (2014.02); *A61M 16/0057* (2013.01); *A61M 16/06* (2013.01); *A61M 16/0605* (2014.02); *A61M 2016/0661* (2013.01)

(58) Field of Classification Search
CPC .............. A61M 16/0057; A61M 16/06; A61M 16/0622; A61M 2016/0661; A61M 16/0605; A61M 61/0611; A62B 23/025
See application file for complete search history.

(56) References Cited

U.S. PATENT DOCUMENTS

| 8,276,588 B1 * | 10/2012 | Connor ................. | A61M 16/06 128/205.25 |
| 2006/0118117 A1 * | 6/2006 | Berthon-Jones ...... | A61M 16/06 128/206.21 |

(Continued)

FOREIGN PATENT DOCUMENTS

| CN | 1681553 A | 10/2005 |
| CN | 101991897 A | 3/2011 |

(Continued)

*Primary Examiner* — Tan-Uyen (Jackie) T Ho
*Assistant Examiner* — Joseph D Boecker
(74) *Attorney, Agent, or Firm* — Michael W. Hass

(57) ABSTRACT

A patient interface device (8) includes a cushion assembly (100) that is customizable to compensate for anatomical variances from patient-to-patient and, therefore, provides an effective seal with the patient's face. The cushion assembly includes a cushion member (102) having a first side structured to engage the patient's face, and a second side disposed opposite the first side, a plurality of plate members (108, 110, 112, 114, 116), and an adjustment mechanism (120, 122, 124). The adjustment mechanism is structured to adjust the position of the plate members, thereby changing the shape of the cushion member to generally conform to the patient's face.

20 Claims, 5 Drawing Sheets

(56) References Cited

U.S. PATENT DOCUMENTS

| | | | | |
|---|---|---|---|---|
| 2007/0215161 | A1* | 9/2007 | Frater | A61M 16/06 128/206.24 |
| 2010/0043798 | A1* | 2/2010 | Sullivan | A61M 16/06 128/205.25 |
| 2010/0071700 | A2 | 3/2010 | Hitchcock | |
| 2011/0232647 | A1* | 9/2011 | Ho | A61M 16/06 128/206.28 |
| 2012/0080035 | A1* | 4/2012 | Guney | A61M 16/06 128/205.25 |

FOREIGN PATENT DOCUMENTS

| | | | |
|---|---|---|---|
| GB | 2475044 | A | 5/2011 |
| WO | WO2004022146 | A1 | 3/2004 |
| WO | WO2008028014 | A2 | 3/2008 |
| WO | WO2008036627 | A1 | 3/2008 |
| WO | WO2010067238 | A1 | 6/2010 |

\* cited by examiner

PATIENT INTERFACE DEVICE WITH CUSTOMIZABLE CUSHION

CROSS-REFERENCE TO RELATED APPLICATIONS

This patent application claims the priority benefit under 35 U.S.C. §371 of international patent application no. PCT/IB2012/057059, filed Dec. 7, 2012, which claims the priority benefit under 35 U.S.C. §119(e) of U.S. Provisional Application No. 61/570,367 filed on Dec. 14, 2011, the contents of which are herein incorporated by reference.

BACKGROUND OF THE INVENTION

1. Field of the Invention

The present invention relates to respiratory patient interface systems, and, in particular, to a respiratory patient interface device including a customizable cushion assembly.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion that rests beneath the patient's nose (such as a "pillows" style nasal cushion having nasal prongs that are received within the patient's nares or a "cradle" style nasal cushion that rests beneath and covers the patient's nares), a nasal/oral mask that covers the nose and mouth, or a full face or "total" mask that covers the patient's face. The patient interface device interfaces the ventilator or pressure support device with the airway of the patient through tubing, so that a flow of breathing gas can be delivered from the pressure/flow generating device to the airway of the patient. It is known to maintain such devices on the face of a wearer by a headgear assembly having one or more straps adapted to fit over/around the patient's head.

Nasal/oral masks, for example, typically include a sealing element or cushion member constructed from a single piece of material that can only offer limited adjustment, for example, by changing the pitch of the mask or cushion member. Most of the adjustments are made by manipulating the headgear assembly attachments and/or a forehead arm. However, anatomical features can vary significantly from one individual to the next. Accordingly, there is no way to effectively and efficiently customize the patient interface device, for example, by shaping or reshaping the cushion member or sealing element to provide a customized, enhanced fit for the patient.

SUMMARY OF THE INVENTION

Accordingly, it is an object of the present invention to provide a patient interface device that overcomes the shortcomings of conventional patient interface devices. This object is achieved according to one embodiment of the invention by providing a patient interface device having a customizable cushion assembly.

It is yet another object of the present invention to provide a method of delivering a flow of breathing gas that does not suffer from the disadvantages associated with conventional techniques. This object is achieved by providing a method that includes employing a customizable cushion assembly to form an effective seal with patient's face, and delivering a flow of breathing gas through a patient interface device.

In one embodiment, a cushion assembly is provided for a patient interface device. The cushion assembly includes a cushion member including a first side structured to engage a patient's face, and a second side disposed opposite the first side, a plurality of plate members, and an adjustment mechanism for adjusting the position of the plate members, thereby changing the shape of the cushion member to generally conform to the patient's face.

A patient interface device for delivering a flow of breathing gas from a flow generating device to an airway of a patient, is also provided. The patient interface device includes a cushion assembly having a cushion member with a first side structured to engage the patient's face, and a second side disposed opposite the first side, a plurality of plate members, and an adjustment mechanism for adjusting the position of the plate members, thereby changing the shape of the cushion member to generally conform to the patient's face.

A method of delivering a flow of breathing gas to a patient, is also provided. The method comprises: providing a patient interface device including a cushion assembly, adjusting the cushion assembly to form a seal with the patient's face, generating the flow of breathing gas, and delivering the flow of breathing gas to the patient interface device. The cushion assembly includes a cushion member including a first side structured to engage the patient's face, and a second side disposed opposite the first side, a plurality of plate members, and an adjustment mechanism for adjusting the position of the plate members, thereby changing the shape of the cushion member to generally conform to the patient's face.

These and other objects, features, and characteristics of the invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 2:
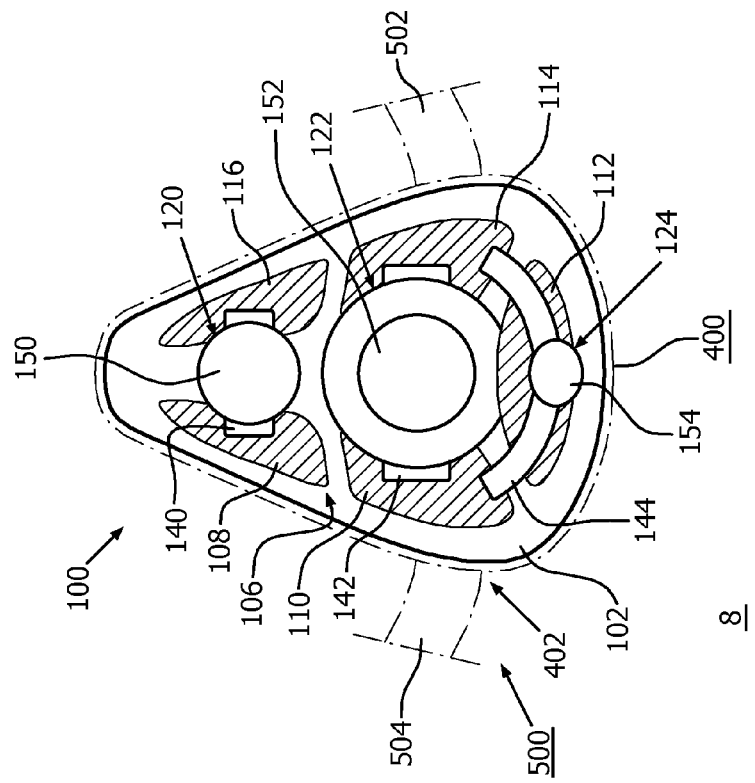
FIG. 2 is a front elevation view of a patient interface device forming a part of the system of FIG. 1.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "connected," "attached" and "directly coupled" mean that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
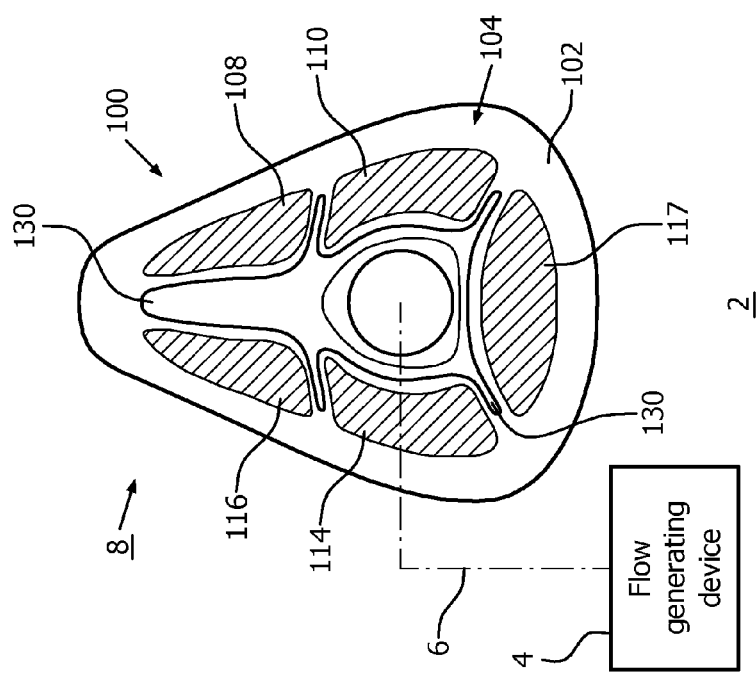
FIG. 1 is a simplified view of a system adapted to provide a regimen of respiratory therapy to a patient according to one exemplary embodiment of the invention.

A system 2 adapted to provide a regimen of respiratory therapy to a patient according to one exemplary embodiment is generally shown in FIG. 1. System 2 includes a flow generating device 4, a delivery conduit 6, and a patient interface device 8. Flow generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and autotitration pressure support devices. Conduit 6 is structured to communicate the flow of breathing gas from flow generating device 4 to patient interface device 8 through conduit 6. Conduit 6 and patient interface device 8 are often collectively referred to as a patient circuit.

In FIGS. 1 and 2, patient interface device 8 is a nasal/oral mask. However, other types of patient interface devices, such as, for example and without limitation, a full face mask, which facilitates the delivery of the flow of breathing gas to the airway of a patient, may be alternatively employed, without departing from the scope of the present invention.

Cushion assembly 100 includes a cushion member 102 having a first side 104 (FIG. 1) structured to engage a patient's face, and a second side 106 (FIG. 2) disposed opposite first side 104. Cushion assembly 100 further includes a plurality of plate members 108, 110, 112, 114, 116 (five are shown in the non-limiting example of FIGS. 1 and 2), and an adjustment mechanism 120, 122, 124 for adjusting the position of plate members 108, 110, 112, 114, 116, thereby changing the shape of cushion member 102 to generally conform to the patient's face.

In an exemplary embodiment, plate members 108, 110, 112, 114, 116 are made from a generally rigid material such as, for example and without limitation, polycarbonate plastic. Cushion member 102 is made from a generally resilient material such as, for example and without limitation, silicone. In an exemplary embodiment, generally rigid plate members 108, 110, 112, 114, 116 are over-molded with the resilient material (e.g., without limitation, silicone) of cushion member 102. Accordingly, it will be appreciated that a "floating structure" is created, wherein plate members 108, 110, 112, 114, 116 correspond to different anatomical features on the patient's face that may require more specific adjustment. In other words, plate members 108, 110, 112, 114, 116 give support and shape to the mask while the silicone or other suitable resilient material of cushion 102 acts as the sealing element, as well as to "suspend" and support plate members 108, 110, 112, 114, 116.

As shown in FIG. 1, plate members 108, 110, 112, 114, 116 are spaced apart from one another, thereby forming a groove 130 in cushion member 102, between adjacent plate members (see, for example, groove 130 between adjacent plate members 108 and 116). It will be appreciated that the groove 130 can, therefore, function as a preload feature to give cushion member 102 the desired shape and resiliency to form an effective seal with the patient's face. Adjustment mechanisms 120, 122, 124 move plate members 108, 110, 112, 114, 116 towards or away from each other to change the basic shape of the mask, as desired, as well as to add rigidity to the suspended plate members.

In the non-limiting example embodiment of FIG. 2, three adjustment mechanisms 120, 122, 124 are employed, wherein each adjustment mechanism 120, 122, 124 includes a number of connecting members 140, 142, 144 and a securing mechanism 150, 152, 154, respectively. Connecting member 140 connects plate members 108,116 together, and includes securing mechanism 150. Adjustment mechanism 122 includes connecting member 142 connecting plate members 110, 114 together, and securing mechanism 152. Adjustment mechanism 124 includes connecting member 144, which connects plates 110, 112 and 114, and securing mechanism 154. By way of example, in operation connecting member 140 is adjustable to move plate members 108,116, thereby changing the spacing of groove 130 disposed therebetween. Securing mechanism 150 is employed to secure connecting member 140 and the corresponding plate members 108, 116 in the desired position. In this manner, all of the plate members 108, 110, 112, 114, 116 can be suitably adjusted to customize the shape of cushion member 102 to form an optimal seal with the patient's face.

Figure 3:
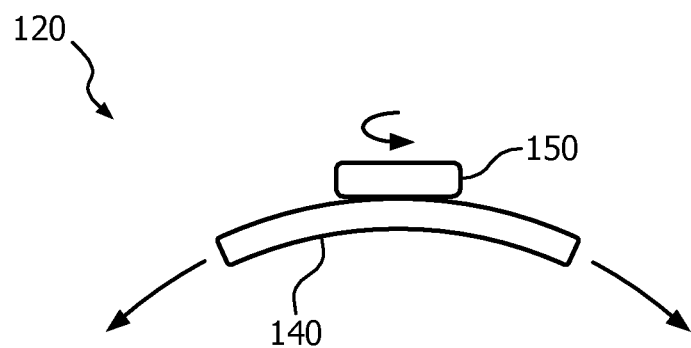
FIG. 3 is a bottom plan view of a cushion assembly for the patient interface device of FIG. 2.
Figure 4:
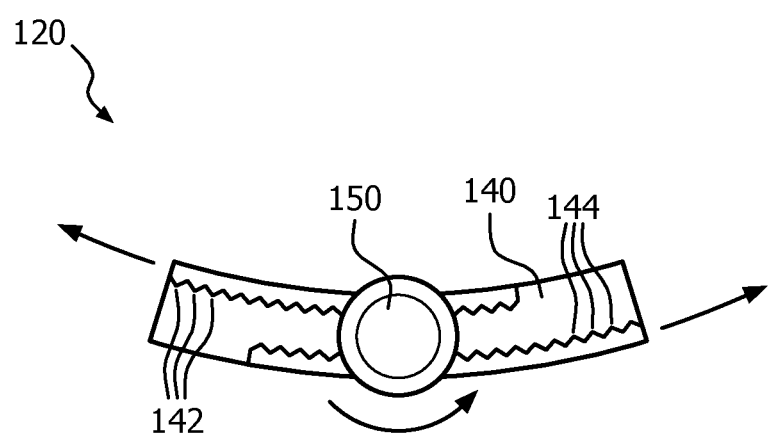
FIG. 4 is a back elevation view of the cushion assembly of FIG. 3.

FIGS. 3 and 4 show isolated views of adjustment mechanism 120 of the aforementioned cushion assembly 100. Specifically, in the non-limiting example embodiment shown, connecting member 140 is an elongated member having a plurality of teeth 142,144, and securing mechanism 150 is a knob or ratchet member structured to engage teeth 140, 142 of elongated member 140 to tighten or loosen elongated member 140 and secure it in the desired position.

Referring again to FIG. 2, it will be appreciated that patient interface device 8 may optionally further include a frame member 400 coupled to second side 106 of cushion member 102. For example and without limitation, frame member 400 may include an attachment portion 402, which is structured to be attached to a suitable headgear assembly 500 for securing patient interface device 8 to the patient's face. For example, frame member 400 (partially shown in phantom line drawing in simplified form in FIG. 2) includes attachment portion 402 structured to adjustably receive strap members 502,504 (partially shown in phantom line drawing in FIG. 2), which can be employed to secure patient interface device 8 in the desired position on patient's face.

Figures 5, 6:
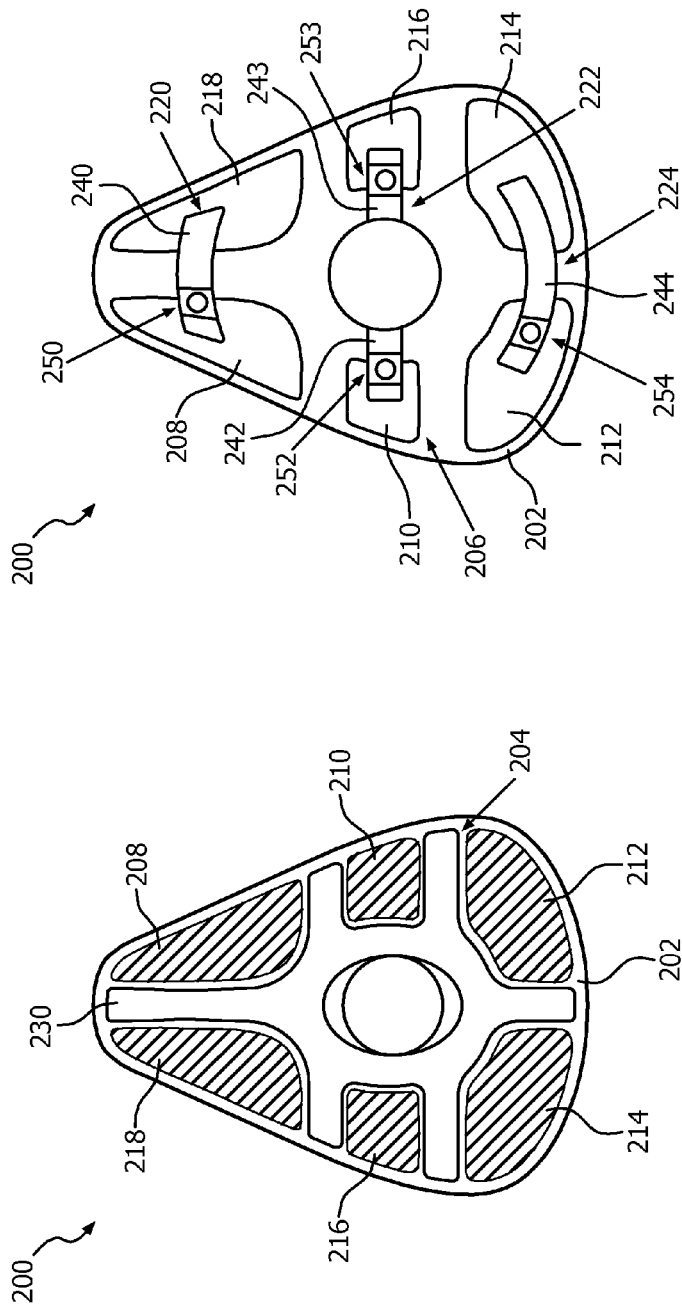
FIG. 5 is a back elevation view of a patient interface device and cushion assembly therefor, in accordance with another exemplary embodiment of the invention.
FIG. 6 is a front elevation view of a patient interface device and cushion assembly therefor of FIG. 5.

FIGS. 5 and 6 show another non-limiting example embodiment of a cushion assembly 200, in accordance with the present invention. Cushion assembly 200 includes cushion member 102 having a first side 204 (FIG. 5) and an opposing second side 206 (FIG. 6). Six plate members 208, 210, 212, 214, 216, 218 are suspended by cushion member 202. A groove 230 is formed between adjacent plate members (see, for example, groove 230 adjacent plate members 208,218), as shown in FIG. 5. As shown in FIG. 6, plate members 208, 218 are connected by connecting member or strap 240 of adjustment mechanism 220. In the non-limiting example of FIG. 6, the securing mechanism is a buckle 250 disposed on connecting member or strap 240 and structured to secure connecting member 240 and plate members 208, 218 in the desired position. Plate members 210 and 216 are connected to the central hub of the mask by connecting members or straps 242, 243, each of which includes a buckle 252, 253, as shown. Similarly, plate members 212, 214 are connected by strap 244, and are adjusted and secured by buckle 254.

Figure 7:
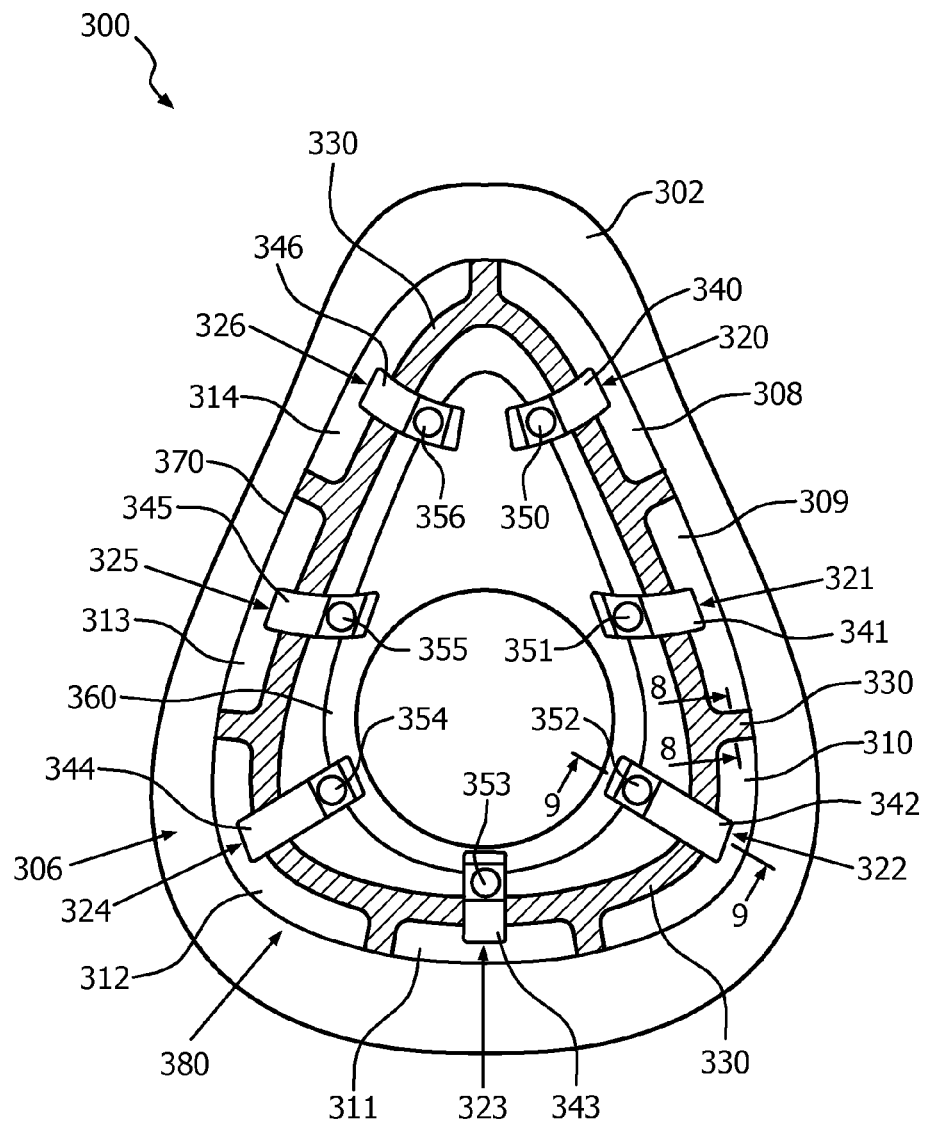
FIG. 7 is a front elevation view of a patient interface device and cushion assembly therefor, in accordance with another exemplary embodiment of the invention.

FIG. 7 shows another non-limiting alternative embodiment of a cushion assembly 300, wherein cushion member 302 further includes a generally rigid center piece 360. Center piece 360 is disposed in the interior of cushion member 302. Cushion member 302 further includes a perimeter and a sealing flap 370 disposed on the first side 204 of cushion member 302 proximate the perimeter. Plate members 308, 309,310, 311, 312, 313,314 (seven are shown in the example of FIG. 7) are directly coupled to sealing flap 370 to form an outer adjustment ring 380 that generally extends around center piece 360, as shown. A groove 330 is formed between center piece 360 and outer adjustment ring 380. The adjustment mechanism comprises a number of adjustment assemblies 320, 321, 322, 323, 324, 325, 326 (seven are shown in FIG. 7), each of which extends between center piece 360 and a corresponding one of plate members 308, 309,310, 311, 312, 313,314, as shown.

Figure 8:
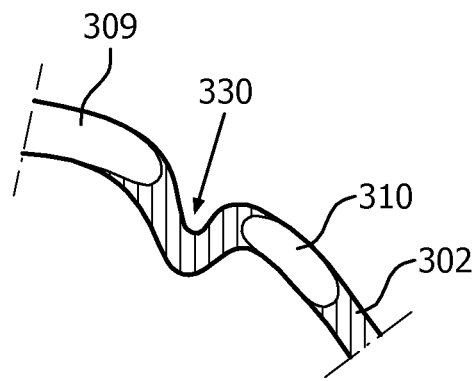
FIG. 8 is a section view taken along line 8-8.

Groove 330 is best shown in FIG. 8, which shows a portion of cushion member 302, in section view. Groove 330 is disposed between adjacent plate members 309 and 310. It will be appreciated that the position of plate members 309, 310 can be adjusted with respect to each other, thereby adjusting the spacing of groove 330 and thus the overall shape of cushion 302 to conform to the patient's face, as desired. It will further be appreciated that in the example shown and described herein, groove 330 is disposed in a spread apart or "open" position wherein plate members (e.g., without limitation, 309, 310) are spaced apart as far as cushion member 302 will allow. Accordingly, groove 330 functions like a spring to hold plate members 309, 310 apart.

Adjustment assembly (e.g., without limitation, 322) allows the patient to pull plate members 309, 310 closer together for adjustment. It will also be appreciated that the reverse spring effect is also possible, in accordance with the present invention. Under such circumstances groove 330 would hold plate members 309,310 in tension, as close together as cushion member 302 would allow, and adjustment mechanism 322 would be used to push plate members 309, 310 apart. Thus, groove 330 functions as a preload mechanism. Therefore, the assembly also has a convenient "reset" function, wherein if adjustment mechanism 322, for example, is released, plate members 309, 310, for example, and cushion member 302, will return to a distinct starting position. Of course, a less structured groove (not shown) could be employed if such preload and/or reset functions are not desired.

Figure 9:
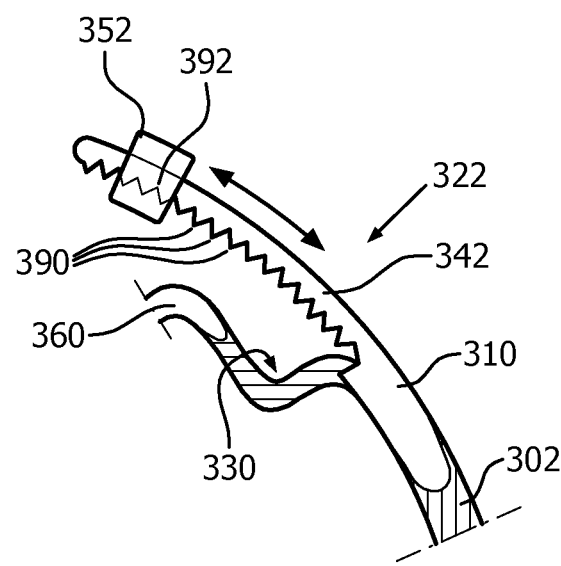
FIG. 9 is a section view taken along line 9-9.

FIG. 9 shows a section view of a portion of cushion member 302, plate members 310, center piece 360 and adjustment assembly 322 for performing the aforementioned adjustment. In the non-limiting example of FIG. 9, adjustment assembly 322 includes elongated connecting member 342 and ratchet member 352, which is disposed thereon. Elongated connecting member 342 includes a plurality of teeth 390. Ratchet member 352 includes corresponding teeth 392 (shown in hidden line drawing in FIG. 9). Accordingly, in operation, ratchet member 352 can be adjusted with respect to elongated connecting member 342 to move plate member 310 toward or away from center piece 360 to suitably adjust the spacing and shape of groove 330. Engagement of teeth 390 with teeth 392 functions to secure adjustment assembly 322 in the desired position.

Accordingly, the present invention provides a cushion assembly 100 (FIGS. 1 and 2), 200 (FIGS. 5 and 6), 300 (FIG. 7) employing generally rigid plate members 108, 110, 112, 114, 116 (FIGS. 1 and 2), 208, 210, 212, 214, 216, 218 (FIGS. 5 and 6), 308, 309, 310, 311, 312, 313, 314 (FIG. 7) suspended by a generally resilient material (e.g., without limitation, silicone), wherein the plate members are directly adjustable to generally conform to the facial features of a patient and create a customized, effective seal between cushion member 102 (FIGS. 1 and 2), 202 (FIGS. 5 and 6), 302 (FIG. 7) and the patient's face.

It can thus be appreciated that the present invention provides a patient interface device that provides a customizable cushion assembly that allows the assembly to be custom tailored to the patient to provide an improved seal with the patient's face.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A cushion assembly for a patient interface device, the cushion assembly comprising:
   a cushion member including a first side structured to engage a patient's face, and a second side disposed opposite the first side;

at least three plate members, the plate members being spaced apart from one another, thereby forming a groove in the cushion member between adjacent plate members; and an adjustment mechanism for adjusting the position of the plate members, thereby changing the shape of the cushion member to generally conform to the patient's face, wherein the adjustment mechanism comprises a number of connecting members each connecting a plurality of the plate members together and including a securing mechanism, wherein the connecting members are adjustable to move the plate members, thereby changing the spacing of the groove disposed therebetween; and wherein the securing mechanism secures the connecting member and the corresponding plate members in the desired position.

2. The cushion assembly of claim 1, wherein the plate members are generally rigid, wherein the cushion member is made from a resilient material; and wherein the generally rigid plate members are over-molded with the resilient material of the cushion member.

3. The cushion assembly of claim 1, wherein the connecting members are straps; and wherein the securing mechanism is a buckle.

4. The cushion assembly of claim 1, wherein the adjustment mechanism is a ratchet assembly, wherein the connecting member is an elongated member having a plurality of teeth, and wherein the securing mechanism is structured to engage the teeth of the elongated member to tighten or loosen the elongated member.

5. A patient interface device for delivering a flow of breathing gas from a flow generating device to an airway of a patient, comprising the cushion assembly of claim 1.

6. The patient interface device of claim 5, wherein the connecting members are straps; and wherein the securing mechanism is a buckle.

7. The patient interface device of claim 5, wherein the adjustment mechanism is a ratchet assembly, wherein the connecting member is an elongated member having a plurality of teeth, and wherein the securing mechanism is structured to engage the teeth of the elongated member to tighten or loosen the elongated member.

8. The patient interface device of claim 5, further comprising a generally rigid center piece disposed in the interior of the cushion member, wherein the cushion member further includes a perimeter and a sealing flap disposed on the first side of the cushion member proximate the perimeter, wherein the plate members are directly coupled to the sealing flap to form an outer adjustment ring that generally extends around the center piece, wherein a second groove is formed between the center piece and the outer adjustment ring; and wherein the adjustment mechanism comprises a number of adjustment assemblies each extending between the center piece and a corresponding one of the plate members.

9. The patient interface device of claim 5, further comprising a frame member coupled to the second side of the cushion member, and wherein the frame member includes an attachment portion structured to be attached to a head gear for securing the patient interface device to the patient's face.

10. A cushion assembly for a patient interface device, the cushion assembly comprising:

a cushion member including a first side structured to engage a patient's face, and a second side disposed opposite the first side;

a plurality of plate members, the plate members being spaced apart from one another, thereby forming a groove in the cushion member between adjacent plate members;

an adjustment mechanism for adjusting the position of the plate members, thereby changing the shape of the cushion member to generally conform to the patient's face, wherein the adjustment mechanism comprises a number of connecting members each connecting a plurality of the plate members together and including a securing mechanism, wherein the connecting members are adjustable to move the plate members, thereby changing the spacing of the groove disposed therebetween; and wherein the securing mechanism secures the connecting member and the corresponding plate members in the desired position; and a generally rigid center piece disposed in the interior of the cushion member, wherein the cushion member further includes a perimeter and a sealing flap disposed on the first side of the cushion member proximate the perimeter, wherein the plate members are directly coupled to the sealing flap to form an outer adjustment ring that generally extends around the center piece, wherein a second groove is formed between the center piece and the outer adjustment ring; and wherein the adjustment mechanism comprises a number of adjustment assemblies each extending between the center piece and a corresponding one of the plate members.

11. The cushion assembly of claim 10, wherein the plate members are generally rigid, wherein the cushion member is made from a resilient material; and wherein the generally rigid plate members are over-molded with the resilient material of the cushion member.

12. The cushion assembly of claim 10, wherein the adjustment mechanism is a ratchet assembly, wherein the connecting member is an elongated member having a plurality of teeth, and wherein the securing mechanism is structured to engage the teeth of the elongated member to tighten or loosen the elongated member.

13. A patient interface device for delivering a flow of breathing gas from a flow generating device to an airway of a patient, comprising the cushion assembly of claim 10.

14. The patient interface device of claim 13, wherein the adjustment mechanism is a ratchet assembly, wherein the connecting member is an elongated member having a plurality of teeth, and wherein the securing mechanism is structured to engage the teeth of the elongated member to tighten or loosen the elongated member.

15. The patient interface device of claim 13, further comprising a generally rigid center piece disposed in the interior of the cushion member, wherein the cushion member further includes a perimeter and a sealing flap disposed on the first side of the cushion member proximate the perimeter, wherein the plate members are directly coupled to the sealing flap to form an outer adjustment ring that generally extends around the center piece, wherein a second groove is formed between the center piece and the outer adjustment ring; and wherein the adjustment mechanism comprises a number of adjustment assemblies each extending between the center piece and a corresponding one of the plate members.

16. The patient interface device of claim 13, further comprising a frame member coupled to the second side of the cushion member, and wherein the frame member includes an attachment portion structured to be attached to a head gear for securing the patient interface device to the patient's face.

17. A cushion assembly for a patient interface device, the cushion assembly comprising:
- a cushion member including a first side structured to engage a patient's face, and a second side disposed opposite the first side;
- a plurality of plate members, the plate members being spaced apart from one another, thereby forming a groove in the cushion member between adjacent plate members, at least one of the plate members being generally planar in shape; and
- an adjustment mechanism for adjusting the position of the plate members, thereby changing the shape of the cushion member to generally conform to the patient's face, wherein the adjustment mechanism comprises a number of connecting members each connecting a plurality of the plate members together and including a securing mechanism, wherein the connecting members are adjustable to move the plate members, thereby changing the spacing of the groove disposed therebetween; and wherein the securing mechanism secures the connecting member and the corresponding plate members in the desired position.

18. The cushion assembly of claim 17, wherein the plate members are generally rigid, wherein the cushion member is made from a resilient material; and wherein the generally rigid plate members are over-molded with the resilient material of the cushion member.

19. The cushion assembly of claim 17, wherein the adjustment mechanism is a ratchet assembly, wherein the connecting member is an elongated member having a plurality of teeth, and wherein the securing mechanism is structured to engage the teeth of the elongated member to tighten or loosen the elongated member.

20. The cushion assembly of claim 17, further comprising a generally rigid center piece disposed in the interior of the cushion member, wherein the cushion member further includes a perimeter and a sealing flap disposed on the first side of the cushion member proximate the perimeter, wherein the plate members are directly coupled to the sealing flap to form an outer adjustment ring that generally extends around the center piece, wherein a second groove is formed between the center piece and the outer adjustment ring; and wherein the adjustment mechanism comprises a number of adjustment assemblies each extending between the center piece and a corresponding one of the plate members.

\* \* \* \* \*